(12) United States Patent
Jacquet

(10) Patent No.: US 11,123,356 B2
(45) Date of Patent: Sep. 21, 2021

(54) **METHODS OF USE FOR OENOTHEIN A AND B FROM *EPILOBIUM* SPECIES**

(71) Applicant: EPILOBIUM, INC., San Diego, CA (US)

(72) Inventor: Robert Jacquet, San Diego, CA (US)

(73) Assignee: Epilobium, Inc., San Diego, CA (US)

( * ) Notice: Subject to any disclaimer, the term of this patent is extended or adjusted under 35 U.S.C. 154(b) by 0 days.

(21) Appl. No.: 15/917,371

(22) Filed: Mar. 9, 2018

(65) Prior Publication Data

US 2018/0256619 A1    Sep. 13, 2018

Related U.S. Application Data

(60) Provisional application No. 62/469,355, filed on Mar. 9, 2017, provisional application No. 62/469,435, filed on Mar. 9, 2017.

(51) Int. Cl.
| | | |
|---|---|---|
| *A61K 31/7034* | (2006.01) | |
| *A61P 13/10* | (2006.01) | |
| *A61K 9/48* | (2006.01) | |
| *A61K 9/00* | (2006.01) | |
| *A61K 9/08* | (2006.01) | |

(52) U.S. Cl.
CPC ........ *A61K 31/7034* (2013.01); *A61K 9/0053* (2013.01); *A61K 9/08* (2013.01); *A61K 9/4891* (2013.01); *A61P 13/10* (2018.01)

(58) Field of Classification Search
CPC ............................. A61K 31/7034; A61P 13/10
See application file for complete search history.

(56) References Cited

U.S. PATENT DOCUMENTS 6,528,490 B2 * 3/2003 Steck ................. A61K 31/7048
424/59
2008/0070877 A1 * 3/2008 Vazquez Gomez .... A61K 31/56
514/169

FOREIGN PATENT DOCUMENTS

WO    WO2016012806    *  1/2016

OTHER PUBLICATIONS

Coulson, S. et al., Complementary Therapies in Medicine, 2013, vol. 21, pp. 172-179 (Year: 2013).*
Lesuisse, D. et al., J. Nat. Prod., "Determination of Oenothein B as the Active 5-alpha-Reductase-Inhibiting Principle of the Folk Medicine Epilobium parviflorum", 1996, vol. 59, pp. 490-492 (Year: 1996).*
Yu, Y. et al., Journal of Urology, "Effects of Steroid Hormones on Morphology and Vascular Endothelial Growth Factor Expression in Female Bladder", 2009, vol. 73, No. 6, pp. 1210-1217 (Year: 2009).*
Faloon, William, Life Extension, "A breakthrough in the relief of overactive bladder and urinary incontinence", Collector's Edition 2009, pp. 167-173 (Year: 2009).*

* cited by examiner

*Primary Examiner* — Bahar Craigo
(74) *Attorney, Agent, or Firm* — DLA Piper LLP (US)

(57) ABSTRACT

The invention provides medicaments comprising an oenothein, including oral formulations to treat inflammation or to treat hormone balance in perimenopausal, menopausal and postmenopausal women. The oenothein for use in such formulations such as oenothein A or oenothein B maybe purified from natural sources, such as *Epilobium*.

6 Claims, 8 Drawing Sheets

EPILOBIUM [Willow Herb] Natural (Unique) Active Ingredients:

2-Alpha-3-Beta-Dihydroxy-Ursolic Acid
2-Alpha-Hydroxy-Ursolic Acid
Alpha Amyrin
Beta Amyrin
Beta Sitosterol
Campesterol
Capric Acid
Ceryl Alcohol
Chamaenerium Tannin
Chamaenerium Tannin IV
Chanerol
Chanerozan
Chlorogenic Acid
Dodecadienoic Acid
Fructose
Glucose
Heneicosan-1-Oic Acid
Heptadecadienoic Acid
Heptadecenoic Acid
Hexadecadienoic Acid
Hexadecenoic Acid
Kaempferol
Lauric Acid
Linoleic Acid
Linolenic Acid
Margaric Acid
Maslinic Acid
Myricetin
Myricetin Glycoside
Myricetin-3-O-Beta-D-Glucuronide
Myristic Acid
Myristoleic Acid
N-Nonacosane
Nonadecanoic Acid
Oenothein A
Oenothein B
Oleanolic Acid
Oleic Acid
Palmitic Acid
Pentadecanoic Acid
Quercetin
Quercetin Glycosides
Sexangularetin
Stearic Acid
Stigmasterol
Sucrose
Tannin
Ursolic Acid

FIG. 3

Section Boisduvalia: Epilobium densiflorum – dense flower willowherb, dense spike-primrose, dense boisduvalia
Epilobium pallidum–large flower spike-primrose
Epilobium pygmaeum–pygmy willowherb, smooth boisduvalia
Epilobium subdentatum (Meyen) Lievens & Hoch
Epilobium torreyi–Torrey's willowherb, brook spike-primrose Section Cordylophorum: Subsection Nuttalia:
Epilobium suffruticosum Nutt. exTorr. & A Gray – shrubby willowherb
Subsection Petrolobium:
Epilobium nevadense Munz – Nevada willowherb
Epilobium nivium Brandegee – Snow Mountain willowherb Section Crossostigma: Epilobium foliosum – leafy willowherb, California willowherb
Epilobium minutum – chaparral willowherb, desert willowherb, small flower willowherb Section Epilobiopsis: Epilobium campestre (Jeps.) Hoch & W.L.Wagner
Epilobium cleistogamum – selfing willow herb Section Macrocarpa: Epilobium rigidum – stiff willowherb, Siskiyou Mountains willowherb Section Xerolobium: Epilobium brachycarpum – tall willowherb, tall annual willowherb, tall fireweed, panicled willow herb Section Zauschneria:
Epilobium canum – Zauschneria, California-fuchsia, hummingbird flower, hummingbird trumpet
Epilobium septentrionale – northern willowherb, Humboldt County fuchsia Section Epilobium:
Epilobium aitchisonii P.H.Raven
Epilobium algidum M.Bieb.
Epilobium alpestre (Jacq) Krock.
Epilobium alsinifolium Vill. – chick weed willowherb
Epilobium alsinoides A. Cunn.
Epilobium alsinoides ssp. alsinoides
Epilobium alsinoides ssp. atriplicifolium (A. Cunn.) P.H. Raven & Engelhorn
Epilobium alsinoides ssp. tenuipes (Hook.f.) P.H. Raven & Engelhorn
Epilobium amurenseHausskn.
Epilobium amurense ssp. amurense
Epilobium amurense ssp. cephalostigma (Hausskn.) C.J. Chen, Hoch & P.H. Raven
Epilobium anagallidifolium – alpine willowherb, pimpernel willowherb
Epilobium anatolicumHausskn.
Epilobium anatolicum ssp. anatolicum
Epilobium anatolicum ssp. prionophyllum (Hausskn.) P.H. Raven
Epilobium angustum (Cheeseman) P.H. Raven &Engelhorn
Epilobium arcticum Sam. – Arctic willowherb
Epilobium astonii (Allan) P.H. Raven & Engelhorn
Epilobium atlanticum Litard. & Maire
Epilobium austral Poeppig & Hausskn.
Epilobium barbeyanumH.Lév.
Epilobium billardierianum Ser. – glabrous willowherb

FIG. 4A

Epilobium billardierianum ssp. billardierianum
Epilobium billardierianum ssp. cinereum (A. Rich.) P.H. Raven & Engelhorn
Epilobium billardierianum ssp. hydrophilum P.H. Raven &Engelhorn
Epilobium billardierianum ssp. intermedium P.H. Raven &Engelhorn
Epilobium bliniiH.Lév.
Epilobium brevifolium D. Don
Epilobium brevifolium ssp. brevifolium
Epilobium brevifolium ssp. trichoneurum (Hausskn.) P.H. Raven
Epilobium brevipesHook.f.
Epilobium brevisquamatum P.H. Raven
Epilobium brunnescens (Cockayne) P.H. Raven &Engelhorn – New Zealand willowherb
Epilobium brunnescens ssp. Beaugleholei K.R.West & P.H.Raven
Epilobium brunnescens ssp. brunnescens
Epilobium brunnescens ssp. minutiflorum (Cockayne) P.H. Raven &Engelhorn
Epilobium capense Buchinger ex Hochst.
Epilobium chionanthum Hausskn.
Epilobium chitralense P.H. Raven
Epilobium chlorifolium Hausskn.
Epilobium ciliatum – fringed willowherb, American willowherb
Epilobium clarkeanum Hausskn.
Epilobium clavatum – talus willowherb, clavate fruit willowherb
Epilobium collinum C. C. Gmelin
Epilobium coloratumBiehler – purple leaf willowherb
Epilobium confertifoliumHook.f.
Epilobium confusumHausskn.
Epilobium conjungensSkottsb.
Epilobium crassumHook.f.
Epilobium curtisiae P.H. Raven
Epilobium cylindricumD.Don
Epilobium davuricumFisch. exHornem. – Daurian willowherb
Epilobium densifoliumHausskn.
Epilobium denticulatum Ruiz &Pav.
Epilobium detzneranumSchltr. ex Diels
Epilobium dodonaei Han Magnoliopsida
Epilobium duriaei Gay ex Godr.
Epilobium fangii C.J. Chen, Hoch &P.H. Raven
Epilobium fastigiatoramosumNakai
Epilobium faurieiH.Lév.
Epilobium forbesii Allan
Epilobium fragile Sam.

FIG. 4B

Epilobium frigidumHausskn.
Epilobium fugitivum P.H. Raven &Engelhorn
Epilobium gemmascens C.A. Mey
Epilobium glabellum G. Forst. – smooth spike-primrose
Epilobium glaberrimum – glaucous willowherb
Epilobium glaciale P.H. Raven
Epilobium glaucum Phil.
Epilobium gouldii P.H. Raven
Epilobium gracilipes Kirk
Epilobium griffithianumHausskn.
Epilobium gunnianumHausskn.
Epilobium halleanum – glandular willowherb
Epilobium hectoriiHausskn.
Epilobium hirsutum – great willowherb, great hairy willowherb, hairy willowherb, codlins-and-cream, apple-pie, cherry-pie
Epilobium hirtigerumA.Cunn.
Epilobium hohuanense S. S. Ying
Epilobium hooglandii P. H. Raven
Epilobium hornemanniiRchb. – Hornemann's willowherb
Epilobium hornemannii ssp. behringianum (Hausskn.) Hoch &P.H. Raven
Epilobium hornemannii ssp. hornemannii
Epilobium howellii – Yuba Pass willowherb, subalpine fireweed
Epilobium indicumHausskn.
Epilobium insulareHausskn.
Epilobium kermodei P.H. Raven
Epilobium keysseri Diels
Epilobium kingdonii P.H. Raven
Epilobium komarovianumH.Lév. – bronzy willowherb
Epilobium lactiflorum – milk flower willowherb, white flower willowherb
Epilobium lanceolatum Sebast. & Mauri – spear-leaved willowherb
Epilobium laxum Royle
Epilobium leiophyllum Hausskn.
Epilobium leptocarpum Hausskn. – slender fruit willowherb
Epilobium leptophyllum – bog willowherb, linear-leaved willowherb
Epilobium luteum Pursh – yellow willowherb
Epilobium macropus Hook.
Epilobium margaretiae Brockie
Epilobium matthewsii Petrie
Epilobium maysillesii Munz
Epilobium melanocaulon Hook.
Epilobium microphyllum A. Rich.
Epilobium minutiflorum Hausskn.

FIG. 4C

Epilobium mirabile Trel. – Olympic Mountain willowherb
Epilobium montanum – broad-leaved willowherb
Epilobium nankotaizanense Yamam. – Nankotaizan willowherb
Epilobium nerteroides A. Cunn.
Epilobium nivale Meyen
Epilobium nummulariifolium R. Cunn. ex A. Cunn.
Epilobium nutans F.W. Schmidt
Epilobium obcordatum – rock fringe willowherb
Epilobium obscurum Schreb. – dwarf willowherb, short-fruited willowherb
Epilobium oreganum – Grants Pass willowherb, Oregon fireweed
Epilobium oregonense – Oregon willowherb
Epilobium pallidiflorum Sol. ex A. Cunn.
Epilobium palustre – marsh willowherb
Epilobium pannosum Hausskn.
Epilobium parviflorum Schreb. – small-flowered willowherb, hoary willowherb
Epilobium pedicellare C. Presl
Epilobium pedunculare A. Cunn. – rockery willowherb
Epilobium pengii C.J. Chen, Hoch &P.H. Raven
Epilobium pernitens Cockayne& Allan
Epilobium perpusillum Hausskn.
Epilobium petraeum Heenan
Epilobium pictum Petrie
Epilobium platystig matosum C.B. Rob.
Epilobium ponticum Hausskn.
Epilobium porphyrium G. Simpson
Epilobium prostratum Warb.
Epilobium psilotum Maire & Sam.
Epilobium pubens A. Rich.
Epilobium puberulum Hook. & Arn.
Epilobium purpuratum Hook.f.
Epilobium pycnostachyum Hausskn.
Epilobium pyrricholophum Franch. & Sav.
Epilobium rechingeri P.H. Raven
Epilobium rhynchospermum Boiss.
Epilobium roseum Schreb. – pale willowherb
Epilobium roseum ssp. consimile (Hausskn.) P.H. Raven
Epilobium roseum ssp. roseum
Epilobium roseum ssp. subsessile (Boiss.) P.H. Raven
Epilobium rostratum Cheeseman
Epilobium rotundifolium G. Forst.
Epilobium royleanum Hausskn.
Epilobium rupicolum Pavlov

FIG. 4D

Epilobium salignum Hausskn.
Epilobium sarmentaceum Hausskn.
Epilobium saximontanum Hausskn. – Rocky Mountain willowherb
Epilobium sikkimense Hausskn.
Epilobium sinense H. Lév.
Epilobium siskiyouense – Siskiyou willowherb, Siskiyou fireweed
Epilobium smithiiH.Lév.
Epilobium staintonii P.H. Raven
Epilobium stereophyllum Fresen.
Epilobium stracheyanum Hausskn.
Epilobium strictumMuhl. – downy willowherb, stiff spike-primrose
Epilobium subalgidum Hausskn.
Epilobium subcoriaceum Hausskn.
Epilobium subnivale Popov ex Pavlov
Epilobium taiwanianum C.J. Chen, Hoch &P.H. Raven
Epilobium tasmanicum Hausskn.
Epilobium tetragonum L. – square-stemmed willowherb
Epilobium tetragonum ssp. lamyi (F.W. Schultz) Nyman
Epilobium tetragonum ssp. tetragonum
Epilobium tetragonum ssp. tournefortii (Michalet) H. Lév.
Epilobium tianschanicum Pavlov
Epilobium tibetanum Hausskn.
Epilobium trichophyllum Hausskn.
Epilobium vernonicum Snogerup
Epilobium wallichianum Hausskn.
Epilobium warakense Nábelek
Epilobium wattianum Hausskn.
Epilobium williamsii P.H.Raven
Epilobium willisii P.H. Raven &Engelhorn
Epilobium wilsonii Cheeseman
Epilobium × wisconsinense Ugent – Wisconsin willowherb (=E. ciliatum ssp. ciliatum × E. coloratum) Chamerion group: Section Chamerion Epilobium angustifolium – fireweed, rosebay willowherb, yanagiran
Epilobium conspersum
Epilobium latifolium – dwarf fireweed, river beauty willowherb
Epilobium speciosum Chamerion group: Section Rosmarinifolium Epilobium colchicum
Epilobium fleischeri
Epilobium stevenii

FIG. 4E

METHODS OF USE FOR OENOTHEIN A AND B FROM *EPILOBIUM* SPECIES

CROSS-REFERENCE TO RELATED APPLICATIONS

This application claims priority under 35 USC § 119(e) to U.S. Application Ser. No. 62/469,355 filed on Mar. 9, 2017 and U.S. Application Ser. No. 62/469,435 filed on Mar. 9, 2017. The disclosure of the prior application is considered part of and is incorporated by reference in the disclosure of this application in its entirety.

BACKGROUND OF THE INVENTION

Field of the Invention

The present invention relates generally to compositions and uses for oenothein, specifically the invention relates to the use of oenothein A and B for the treatment of various disease and disorders.

Background Information

Oenothein is a tannin found in a number of trees, plants and herbs. The natural product oenothein A and B, a dimeric macrocyclic ellagitannin, has a wide range of biological activities, such as antioxidant, anti-microbial anti-inflammatory, antiviral, antifungal, and antitumor.

The present invention is the administration of oenothein ellagitannins specifically oenothein A and B of which is related to compositions and methods for treating urinary incontinence, treating UTI (urinary tract infection); treating hormonal imbalance in perimenopausal, menopausal and postmenopausal women treating female hair loss for perimenopausal, menopausal and postmenopausal women; treating the conversion of testosterone to estrogen (aromatase), in perimenopausal, menopausal and postmenopausal women at risk of having such disorders for women.

Treating cardiovascular disease enhanced with acetylsalicylic acid as a polypill, for men and women. Treating joint pain and minor arthritis enhanced with Sodium Naproxen as a polypill for both men and women.

Treating benign prostatic hyperplasia (BPH) for men, more specifically to the administration of oenothein ellagitannins A and or B, in subjects having or at risk of having such disorders. Treating smooth muscle i.e., detrusor, as it pertains to hormone balance effecting bladder the vascular system and urinary tract.

Oenothein A and B in the production of formulations related maladies identified as Androgenic Alopecia (AGA), hair loss for women (Female Pattern baldness), in a combination with a ingestible, oenothein A and B as a topical application with oenothein B between 0.01%<100% to affected areas of the human scalp or as a prophylactic which is dissolved in suspension with liquid, gel, foam or other topical applications containing melatonin at 0.01 mg/per ml<0.05 mg/per ml, as a topical application for women's hair loss Oenothein A and B extracted using alcohol derived from sugar cane, molasses, vegetable, fruit, grain or other organic plant sources, glycerol extracted from plant sources as glycerol. (Glycerol is a simple polyol compound. It is a colorless, odorless, viscous liquid that is sweet-tasting and non-toxic. The glycerol backbone is found in all lipids known as triglycerides). (See references, Wikipedia), This includes extraction with water, alcohol and water, distilled or reverse osmosis (RO) and or infused with suspended antibacterial, antimicrobial elements including silver sub-nano/nano clusters. "Silver nanoparticles constitute a very promising approach for the development of new antimicrobial systems. Nanoparticulate objects can bring significant improvements in the antibacterial activity of this element, through specific effect such as an adsorption at bacterial surfaces". (See references), Antibacterial activity of silver nanoparticles: A surface science insight 2016, Benjamin Le Ouay Francesco Stellacci. Co2 extraction (critical Co2 extraction). *Epilobium* extracted with alcohol or alcohol and water, were the alcohol is removed or separated mechanically, chemically, gravity, crystallization or with adequate temperature to distill the alcohol into a separate recovery vessel.

Inflammation is the body's attempt at self-protection; the aim being to remove harmful stimuli, including damaged cells, irritants, or pathogens and begin the healing process.

*Epilobium* is a plant used in many countries around the world, for the most part it is used in the treatment of prostate, bladder disorders (all classes) and for the tonification of the urinary tract.

Research has shown that *Epilobium* containing therapeutic levels of oenothein A and B to inhibit the conversion of testosterone to dihydrotestosterone (DHT) by its activity on 5-alpha-reductase and aromatase (the group of enzymes that catalyze the conversion of testosterone to estradiol).

In the United States, the National Association for Continence (NAFC) reported in a nationwide survey conducted in 2002 that nearly one in four women age 20 to 70 years old had incontinence. Incontinence was decreased by inhibiting the aromatase enzyme; it may make more testosterone available to strengthen the pelvic muscles. Authors: Michael Srulevich, DO, MPH, and Anita Chopra, M.D.

Incontinence occurs because of problems with muscles and nerves that help to hold or release urine. The body stores urine, water and wastes removed by the kidneys in the bladder, a balloon-like organ. The bladder connects to the urethra, the tube through which urine leaves the body, 2009 Michigan Institute of Urology. In a study of postmenopausal women, decreased androgen (testosterone) levels weaken the pelvic floor and sphincter muscles, while an estrogen deficit induces atrophy of the urethra (Life Extension Institute 2004).

With ages standardized, the prevalence of urinary incontinence in combined surveys was 51.1% in women and 13.9% in men. Prevalence in women increased from 49.5% in 2001 to 2002, to 53.4% in 2007 to 2008 (Ptrend=0.01) and in men from 11.5% to 15.1%, respectively. (See references), Prevalence and Trends of Urinary Incontinence in Adults in the United States, 2001 to 2008, Alayne Markland, University of Alabama at Birmingham I UAB·Department of Medicine.

Figure 1:
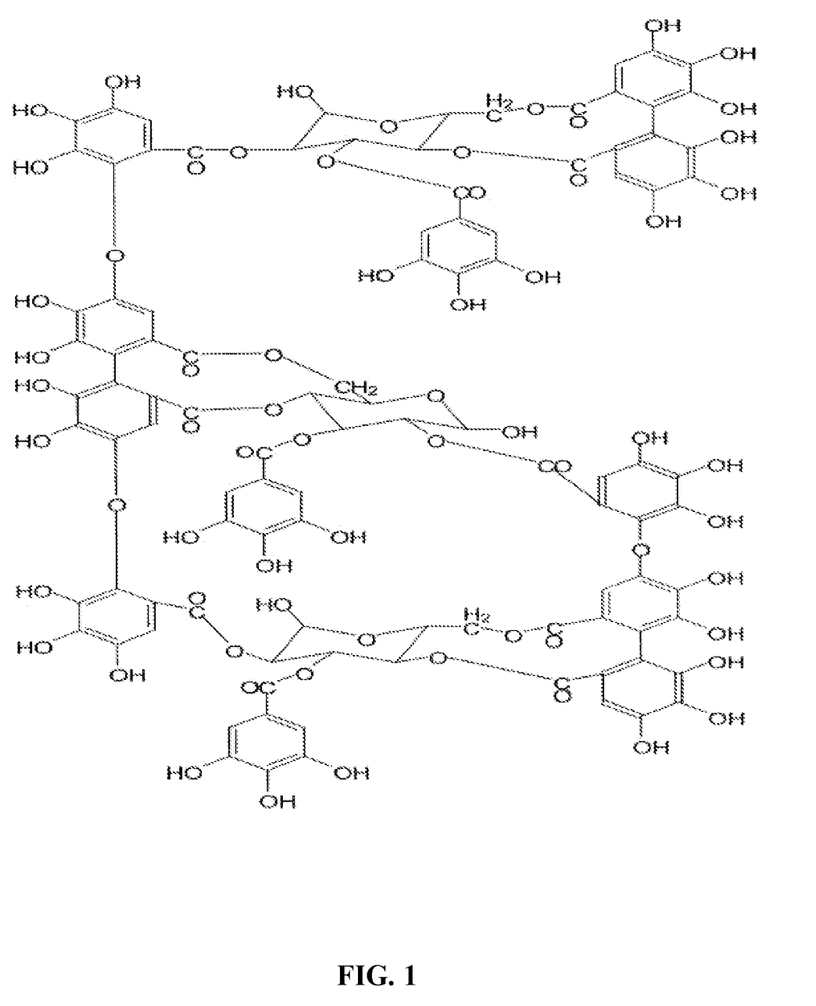
FIG. 1 is a drawing of the known structure of oenothein-A.
Figure 2:
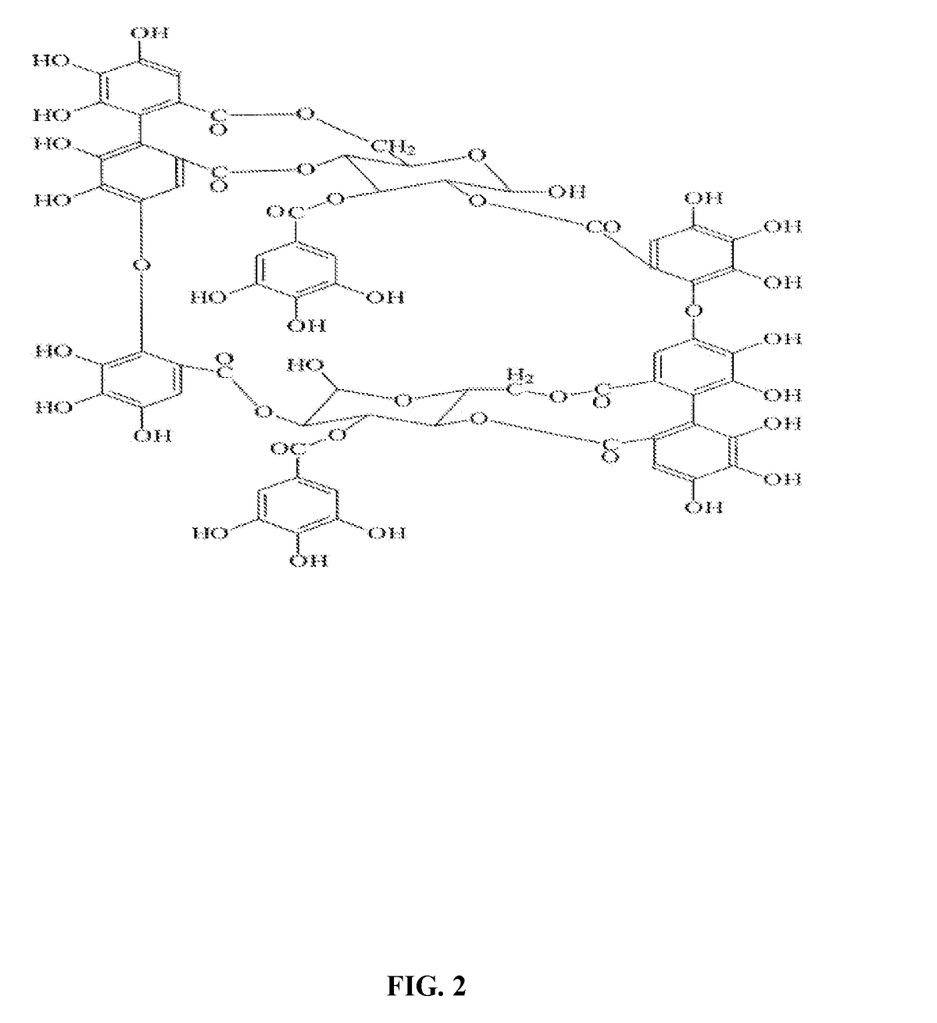
FIG. 2 is a drawing of the known structure of oenothein-B.
Figure 3:
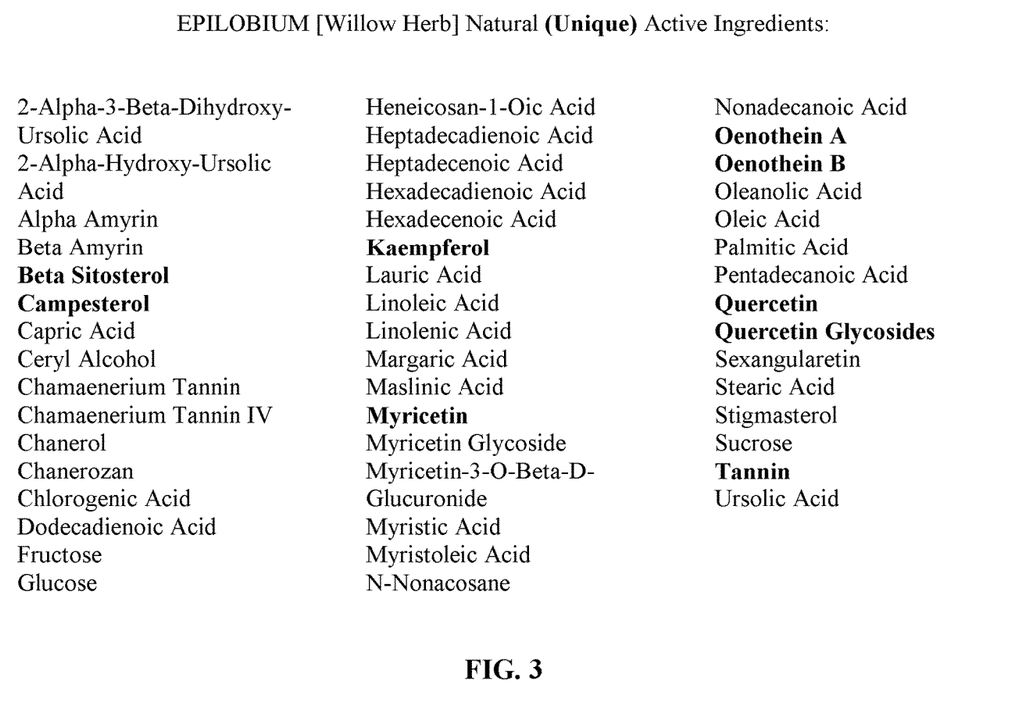
FIG. 3 is a listing of active ingredients particular of *Epilobium Angustifolium* and commonly found in all *Epilobium* species.

A purified aqueous extract was obtained from New World *Epilobium angustifolium* (Canadian Willow herb) and subjected to a variety of analytical techniques, which unambiguously identify the purified compound as oenothein B. This analysis included mass spectroscopy (MS) and nuclear magnetic resonance spectrometry (NMR) as shown in FIGS. 3 through 6.

While oenothein B was found by these methods to be present in solvent-free aqueous extracts of Canadian Willow herb at levels up to 9.6%, myricetin glucuronide—the substance identified as the active ingredient of the anti-inflammatory action of Old World *Epilobium angustifolium* (see FIG. 3, ABSTRACT of INVENTION section herein, pg. 19) was not found in extracts of Canadian Willow herb. U.S. Pat. No. 6,528,490 Mar. 4, 2003.

Ellagitannins are a diverse family of naturally-occurring compounds consisting of a central core of glucose esterified with hexahydroxydiphenic acid. Ellagitannins are known as active constituents of a variety of medicinal plants (Okuda and Hotano, 1989, *Planta Med.* 55 (2): 117). For example, U.S. Pat. No. 5,843,911 issued Dec. 1, 1998 discloses the use of ellagitannins having galloyl and hexahydroxydiphenoyl substituent's as hyaluronidase enzyme inhibitors for topical application, to enhance water retention in skin by preventing the hydrolysis of hyaluronic acid. The ellagitannins disclosed in U.S. Pat. No. 5,843,911 is identified as "GOD-type" ellagitannins, extractable from a variety of plants.

U.S. Pat. No. 5,525,594 issued Jun. 11, 1996 discloses the use of the ellagitannins oenothein-B (which is not a "GOD-type" ellagitannin as defined in U.S. Pat. No. 5,843,911) for the treatment of hyper androgenic disorders by oral, rectal or parenteral administration (also reported in Lesuisse al., 1996, *J. Nat. Prod.* 59(5):490). In this treatment, the mechanism of action of oenothein B is thought to be the inhibition of 5-reductase, an enzyme responsible for the conversion of testosterone to dihydrotestosterone. Both oenothein-A and oenothein-B from *Epilobium* species have been shown to have similar pharmacologic activity, evidenced by 5-reductase and aromatase inhibition (Ducrey et al., 1996, *Planta Medica* 63:111). It is disclosed in U.S. Pat. No. 5,525,594 that oenothein-B may be extracted from various Onagraceae plants (evening-primrose family), including *Epilobium parviflorum*. Ducrey et al., 1996, supra, disclose the extraction of oenothein A and B from *E. capense*, and the quantization of oenothein-B in a variety of old world *Epilobium* species including Old World *E. angustifolium* L (Rosebay Willow herb). The apparent antiviral and antitumor activities of oenothein-B are also discussed by Ducrey et al., 1996, supra, and in U.S. Pat. No. 5,525,594.

Aqueous extracts of Old World *Epilobium angustifolium* have been suggested for use as oral anti-inflammatories (German Patent No. 3,605,250 of Jul. 16, 1987), and the active ingredient in such extracts has been identified as the flavonoids compound myricetin glucuronide (3,3'4',5,5',7-hexahydroxyflavone-3-O-glucuronide; see Hiermann et al., 1991, *Planta Medica* 57:357 and German Patent 3,900,023 of Jul. 12, 1990).

It has previously been disclosed, by the present inventor, that crude aqueous extracts of New World *Epilobium Parviflorum* (Small Willow herb) have anti-inflammatory properties, aromatase inhibition, DHT blocking, inhibit cyclooxygenase-1 and-2(COX-1 and COX-2) catalyzed prostaglandin biosynthesis. (See references), Studies on antibacterial, anti-inflammatory and antioxidant activity of herbal remedies used in the treatment of benign prostatic hyperplasia and prostatitis. 2005 Steenkamp V.

SUMMARY OF THE INVENTION

The invention is based on the seminal discovery that the administration of oenothein A or B is useful for treating a variety of disorders. In one embodiment, the invention provides a method of treating one or more symptoms of overactive bladder in a subject comprising administering to the subject a therapeutically effective amount of oenothein A or B, wherein the one or more symptoms of overactive bladder are selected from the group consisting of frequency of urgency, nocturia, increase in urinary micturition frequency, urinary incontinence, hormone balance for perimenopausal, menopausal and postmenopausal women and inflammation. (See references), Phytochemistry, pharmacology and traditional uses of different *Epilobium* species. (Onagraceae) 2014 Kiss A. In one aspect, the oenothein A or B is formulated in an oral dosage form, such as a capsule which is protected by PH sensitive encapsulation. Oenothein B (OeB) has quite low bio accessibility for oral consumption due to their susceptibility to decomposition both in vitro and in vivo. Herein, the design and synthesis of food-grade polyelectrolyte complex coacervate using case in phosphopeptides (CPPs) and chitosan (CS) to encapsulate OeB for enhanced protection through gastrointestinal (GI) tract. (See references), Rational design of food-grade polyelectrolyte complex coacervate for encapsulation and enhanced oral delivery of oenothein B, Yaqi Lan et al (Oct. 20, 2017)

In another embodiment, the invention provides a composition formulated for oral delivery consisting essentially of oenothein A or B. The composition can be formulated for example in the form with of a pill, capsule, granules, time release capsules, sublingual, buccal, nasally, any form intended to dissolve in the mouth directly or sprayed microparticles, nano particles and liposome's. In a preferred aspect, the composition is formulated for oral delivery in an oral dosage form with regard to sensitivity to PH in the gut. Invention compositions optionally include an agent selected from the group consisting of pharmaceutically acceptable excipient, lubricant, binder, glidant, filler, flavoring agent, masking agent, vitamin, mineral, a carrier and mixtures thereof.

The composition maybe in single dosage form, such as an enteric coated formulation oral liquid oral formulation. In one aspect, the oenothein A or B is formulated for oral delivery in capsular, spray or pill form and contained in a package with instructions for use.

In another embodiment, the invention provides a method of reducing inflammation, treating urinary incontinence, treating bacterial urinary incontinence, treating urinary tract fungal infection, treating hormonal imbalance in perimenopausal, menopausal and postmenopausal women treating female hair loss for perimenopausal, menopausal and postmenopausal, treating the conversion of testosterone to estrogen (via aromatase) in perimenopausal, menopausal and postmenopausal women, to inhibit cyclooxygenase-1 and-2 (COX-1 and COX-2) catalyzed prostaglandin, biosynthesis, comprising administering to a subject in need thereof a therapeutically effective amount of a composition of the invention. Treating smooth muscle as it pertains to hormone balance effecting bladder the vascular system and urinary tract. Treating benign prostatic hyperplasia (BPH) for men, more specifically to the administration of oenothein ellagitannins in subjects having or at risk of having such disorders. (See references), Phytochemistry, pharmacology and traditional uses of different *Epilobium* species (Onagraceae) 2014, Kiss. A, Assessment report on *Epilobium angustifolium* L. and/or *Epilobium parviflorum* Shreb., herba FINAL European Medicines Agency 2015. Composition and antimicrobial activity of the essential oil distilled aromatic water and herbal infusions from *Epilobium parviflorum* Scheb. 2017 Tomas Bajer et al.

In some aspects, the oenothein is extracted or prepared from New World *Epilobium parviflorum* (small willow herb). In one aspect, the oenothein A or B is purified to a concentration of more than <1.0% by weight. In another aspect, the oenothein is extracted or prepared from a plant source other than New World *Epilobium parviflorum*.

BRIEF DESCRIPTION OF THE DRAWINGS

FIG. 4A-4E is a listing of the most commonly known species of *Epilobium* known to the USDA.

DETAILED DESCRIPTION OF THE INVENTION

The present invention is based on the seminal discovery that the administration of oenothein A or B is useful for treating a variety of disorders. It has been surprisingly discovered that oenothein's are potent anti-inflammatories, anti-irritant's and free radical scavengers which inhibit cyclooxygenase-1 and-2 (COX-1 and COX-2) catalyzed prostaglandin biosynthesis, accordingly, the invention provides formulations comprising an oenothein including orally administered for use as free radical scavengers or as prophylactic against damage caused by inflammation, hormone imbalance caused by the normal aging process or imbalance by environmental, biological, pathogenic or other influences. The oenothein for use in such formulations may for example be oenothein A or oenothein B. The oenothein maybe purified from natural sources, such as plant material, or it may be prepared synthetically.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The preferred methods and materials are now described.

Other aspects of the invention include methods of formulating oral medication for treatment of inflammation, irritants or free radical scavengers, comprising adding a known amount of an oenothein A and or B to such compositions (as to be of greater effectiveness we are motivated to determine the amount of oenothein being administered in herbal remedies per malady i.e., as a DHT Blocker or Aromatase Inhibitors), such as in *Epilobium parviflorum* extracts. In light of past and the present inventions, plant extracts for use in such formulations may now be assayed (Sigma Aldrich), to determine the concentration of oenothein B in the extracts so that dosages maybe formulated with a higher level of reliably. For example, New World *Epilobium parviflorum* maybe assayed for oenothein B content. Packaging for formulations of the invention may include text that indicates that the formulations are useful for prophylactic inflammation due to strenuous activity, exposure to free radicals or hormone imbalance, such text may optionally disclose that the formulations contain oenothein B.

In another aspect of the invention some of the known species of *Epilobium* (see diagram 4) contain oenothein and may be orally administered as an anti-inflammatory, free radical scavengers or for treating hormone imbalance. For example, *Epilobium E. rosmarinifolium* and *Epilobium E. angustifolium* may be used for making such extracts where they contain oenothein A or oenothein B or mixtures thereof. It is also contemplated that compositions of the present invention oenothein A and or B can be included into functional food or beverage products (e.g., alcoholic beverages, fortified water, energy drinks, nutritional drinks, vitamins, supplements, functional foods and other ingestible variations) and pharmaceutical products (e.g. pills, injectable solutions). "Supplements" can include vitamins, minerals, herbs or the botanicals, amino acids, enzymes and metabolites. Such supplements can be administered orally.

The terms "mixture," "mix," and "mixing" or any variants of these terms, when used in the claims and/or specification includes, stirring, blending, dispersing, milling, homogenizing, and other similar methods. The mixing of the components or ingredients of the disclosed compositions can form into a solution. In other embodiments, the mixtures may not form a solution. The ingredients/components can also exist as un-dissolved colloidal suspensions.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective" as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The following definitions should not be considered limiting: Aromatase is an enzyme that is responsible for a key step in the biosynthesis of estrogens. Because estrogens also promote certain deadly pathologies and other diseases, aromatase inhibitors are frequently used to treat those diseases. Dihydrotestosterone (DHT) is a biologically active metabolite (byproduct) of the hormone testosterone; it is formed primarily in the prostate gland, testes, hair follicles, and adrenal glands by the enzyme 5-alpha-reductase. 5-alpha-reductaseisanenzyme involved in steroid (androgen and estrogen) metabolism.

In one aspect, the invention provides formulations or medicaments for treating a variety of symptoms, diseases or disorders, including inflammation, such as inflammation and irritation of the urinary tract, to inhibit cyclooxygenase-1 and-2 (COX-1 and COX-2) catalyzed prostaglandin biosynthesis, neuropathy, as an antioxidant for free radical scavenging as a hormone balancing agent, oenothein B has an effect on hair loss for both men and women, hormone balancing for perimenopausal, menopausal and postmenopausal women's hair loss. As an antibacterial a wide variety diseases are treatable with the compounds of the invention, including Escherichia coli is one of the most frequent causes of many common bacterial infections, including cholecystitis, bacteremia, cholangitis, urinary tract infection (UTI) and traveler's diarrhea and other clinical infections such as neonatal meningitis and pneumonia. As an anti-fungal oenothein B interferes with the cell morphology of the fungus Paracoccidiodes brasiliensis, the most prevalent human systemic mycosis in Latin America. (Therapeutic Potential of Polyphenols from *Epilobium angustifolium*, (Fireweed) Igor A. Schepetkin, 2017).

Aromatase inhibition, the conversation of testosterone to estrogen or according to the American Cancer Society (ACS), aromatase inhibitors work differently from tamoxifen and raloxifene. Instead of blocking the estrogen receptors, they stop a key enzyme (called aromatase) from changing other hormones into estrogen; this lowers estrogen levels in the body, taking away the fuel that estrogen receptor-positive breast cancers need to grow. ACS, (Jul. 20, 2013).

In some aspects, the invention provides methods of medical, therapeutic or prophylactic dose of an oenothein is administered, such as by administration of a pharmacologically acceptable formulation. Such formulations of the invention may comprise oenothein A or oenothein B and a pharmacologically acceptable excipient or carrier, and may comprise a pharmaceutically acceptable salt of the oenothein. In some embodiments, such formulations may comprise a therapeutically or prophylactically effective amount sufficient to alter, and preferably inhibit, inflammation or hormone imbalance, or to quench free radicals.

As used herein "pharmaceutically acceptable carrier" or "excipient" includes any and all creams, gels, solvents, dispersion media, sublingual, buccal administration, coatings, antibacterial, antipathogen and antifungal agents, isotonic and absorption delaying agents, and the like that are physiologically compatible and do not significantly adversely affect the pharmaceutical properties (e.g. toxicity and effectiveness) of the oenothein, such as are conventionally used in the cosmetic and pharmaceutical arts. In one embodiment, the carrier is suitable for oral administration. Under some conditions, oenothein's may undergo hydrolysis in acid or base, so that pharmaceutically acceptable carriers or excipients may include pH buffers to maintain an acceptable pH for pharmaceutical activity (See references), Daniel et al., 1991, J. Natural Products 54(4):946, for a discussion of the effects of pH on ellagitannins), (See references), Lan Y 2017 Rational food-grade polyelectrolyte complex coacervate for encapsulation and oral enhanced oral delivery of oenothein B).

A "therapeutically effective amount" refers to an amount effective, at dosages and for periods of time necessary, to achieve the desired therapeutic result, such as reduction or reversal of inflammation or irritation. A therapeutically effective amount of an oenothein may vary according to factors such as the disease state, age, sex, weight of the individual, and the ability of the oenothein to elicit a desired response in the individual. Dosage regimens maybe adjusted to provide the optimum therapeutic response. A therapeutically effective amount is also one in which any toxic or detrimental effects of the oenothein are outweighed by the therapeutically beneficial effects.

A "prophylactically effective amount" refers to an amount effective, at dosages and for periods of time necessary, to achieve the desired prophylactic result, such as preventing or inhibiting the rate of inflammation or irritation or the onset of inflammation or irritation, or quenching of free radicals. A prophylactically effective amount can be determined as described above for the therapeutically effective amount.

In particular embodiments, a preferred range for therapeutically or prophylactically effective amounts of an oenothein maybe 2.5% to 14%<by weight. Dosage values may vary with the severity of the condition. It is to be further understood that for any particular subject, specific dosage regimens maybe adjusted over time according to the individual need and the judgment of the person administering or supervising the administration of the compositions, and that dosage ranges set forth herein are exemplary only and are not intended to limit the scope or practice of the methods of the invention. (See references), Phytochemistry, pharmacology and traditional uses of different species. (Onagraceae) 2014 Kiss.

In accordance with another aspect of the invention, therapeutic compositions of the present invention, comprising an oenothein, maybe provided in container labels that provide instructions for use of the formulation to: treat inflammation, hormone imbalance, scavenge free radicals, urinary incontinence. The labels may also disclose that the compositions comprise an oenothein.

It has previously been disclosed, by the present inventor, that crude aqueous extracts of *Epilobium Parviflorum* have anti-inflammatory, hormone balancing and free radical scavenging properties when taken orally. In accordance with the present invention the concentration of oenothein B in such extracts exceed <5% by weight. Accordingly, with the unexpected discovery that oenothein B is an active ingredient in such extracts, the present invention provides for novel formulations of *Epilobium Parviflorum* or other *Epilobium* species extracts having oenothein B concentrations in excess of <5%. In alternative aspects, the present invention provides formulations for treating inflammation, hormone imbalance or free radical scavenging that are prepared from purified oenothein B obtained from *Epilobium Parviflorum* or other *Epilobium* species, where the oenothein B is purified to a concentration of greater than <5% prior to formulation. In alternative embodiments, purified oenothein B from *Epilobium Parviflorum* or other *Epilobium* species may be utilized in the present invention in concentrations ranging from 1%< up to concentrations of approximately 100%.

A variety of methods may be used to purify oenothein from natural sources for use in the various aspects of the present invention. For example, U.S. Pat. No. 5,525,594 (incorporated herein by reference) discloses methods of preparing oenothein B from plants. Similarly, Ducrey et al., 1996, supra disclose oenothein A and oenothein B purification and characterization methods (incorporated herein by reference). Alternative purification methods may be used in accordance with the present invention, provided that they may be used to produce a pharmaceutically acceptable preparation of purified oenothein B suitable for use in the various aspects of the present invention.

Presented below are examples discussing the administration of oenothein A or B contemplated for the discussed applications. The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example 1

Isolation and Purification of Oenothein B

A purified aqueous extract was obtained from New World *Epilobium angustifolium* (Canadian Willow herb) and subjected to a variety of analytical techniques, which unambiguously identify the purified compound as oenothein B. This analysis included mass spectroscopy and nuclear magnetic resonance spectrometry. While oenothein B was found by these methods to be present in solvent-free aqueous extracts of Canadian Willow herb at levels up to 9.6%, myricetin glucuronide—the substance identified as the active ingredient of the anti-inflammatory action of Old World *Epilobium angustifolium* (U.S. Pat. No. 6,528,490B2, see the Background section herein)—was not found in extracts of Canadian Willow herb.

Example 2

Efficacy of Oenothein B to Treat Inflammation and Irritation

This example shows the effectiveness of the purified oenothein B characterized in Example 1 in treating inflammation and irritation.

In the hen's-egg chorioallantoic membrane (CAM) model, in which the CAM is treated with 15% lactic acid as a standard irritant, the development of manifestations of membrane irritation were tracked and scored according to published methods for assessing irritancy (Luepke and Kemper, 1986, *Food and Chemical Toxicology* 24: 495; Spielmann et al. 1997, *Food and Chemical Toxicology* 35:39). A sample of the oenothein B extract from Canadian Willow herb described in Example 1 was tested at a 1% (weight to volume) dilution for activity in the CAM model. The results showed a decrease in irritation by up to 70% when the oenothein B was applied before the irritant (simulating a prophylactic use) while an 80% decrease was seen with the whole aqueous extract itself.

Further testing was performed with whole aqueous extract of Canadian Willow herb and a whole extract sample spiked with 10% additional oenothein B. The results showed an increase in the reduction of irritation by the spiked sample of 19% over that of the whole extract by itself.

In human skin patch tests, an oenothein B extract from Canadian Willow herb formulated in a lotion ameliorated the irritant effects of 15% lactic acid, as measured after 0.5, 1, 4 and 24 hours, compared to controls with no treatment, treatment with water and treatment with the lotion alone (containing no extract).

Example 3

Free Radical Scavenging Activity of Oenothein B

This example shows the free radical scavenging activity of oenothein B. A sample of the oenothein B extract from Canadian Willow herb described in Example 1 was assessed using the xanthine oxidase/acetaldehyde spectro photometric method, in which superoxide radical ions regenerated in vitro using acetaldehyde and xanthine oxidase, in the presence of test compounds (Fridovich, 1970, *Journal of Biological Chemistry* 245:4053; Hodgson and Fridovich, 1976, *Biochimicaet Biophysica Acta* 430:182). The scavenging of free super oxide radicals is quantitated spectrometrically and expressed in terms of percentage of radicals scavenged. Assays were performed with 1% (w/v) and 0.1% (w/v) dilutions of the dried extract, which yielded up to 100% scavenging activity and up to 99% scavenging activity respectively.

Example 4

Quantifying Oenothein B

This example shows *Epilobium parviflorum* using a method of quantifying oenothein B using Gallic Acid (Hydrolyzed) and Gallic Acid (Free) (14). Improved and Validated HPTLC Method for Quantification of oenothein B and its Use for Analysis of *Epilobium angustifolium* L. Alexander N. Shikov*, Olga N. Pozharitskaya, Svetlana A. Ivanova, Valery G. Makarov, Vladimir P. Tikhonov, and Bertalan Galambosi. After using the Gallic Acid method on *Epilobium Parviflorum* the following values were recorded 0.0074, 0.0087 and 0.0096. Ellagitannins are usually separated and characterized by HPLC, HPLC-MS, MALDI-TOF-MS, and HPTLC [17-20]. There is currently a method for using oenothein B through a marker made available by Sigma Aldrich.

Example 5

Efficacy of *Epilobioum Parviflorum* Extract on Prostate Inflammation

This example shows the effectiveness of 200 mg sample of *Epilobium parviflorum* extracted with sugar cane alcohol and purified water. A study was done with a difficult elderly population in generally poor health, with the participants taking multiple prescription medications. The average age of the participants was (82 years of age). In spite of this, the results were quite remarkable in that 55.6% (5 out of 9) improved significantly, with an average improvement of 48.11%, 11.1% (1 out of 9) showed no change, 33.3% (3 out of 9) worsened with an average worsening of 19.7%. Given this difficult sample it is likely that this population would have worsened anyway with or without intervention. The focus of the study was prostate inflammation causing frequent trips to the bathroom. All the patients were under the care of Dr. Daniel L. Johnson, M.D., Desert Longevity Institute, Palm Desert, Calif., *Epilobium* Study for BPH on Geriatric Patients Jul. 13, 2013, (ref. Vitalone et al., 2002-2003, Durcey et al. 1997).

Those of skill in the art should, in light of the present disclosure, appreciate that many changes can be made in the specific embodiments which are disclosed and still obtain alike or similar result without departing from the spirit and scope of the invention. The present invention is not to be limited in scope by the specific embodiments described herein, which are intended as illustrations of individual aspects of the invention, and functionally equivalent methods and components are within the scope of the invention. Indeed, various modifications of the invention, in addition to those shown and described herein, will become apparent to those skilled in the art from the foregoing description. Accordingly, the invention is limited only by the following claims.

REFERENCES

1. Aoki, K. et al. (1995), Biochem Biophys Res Commun, A Macro circular Ellagitannin, Oenothein B., Suppresses Mouse Mammary Tumor Gene Expression via Inhibition of Poly(ADP-ribose)Glycohydrolase, 210(2): 329-37.
2. Dijkstra et al. (1996). "Repertorium 96/97" SDUServicecentrumUitgeveverijen.
3. Ducrey et al. "Inhibition of 5-alpha-reductaseandaromatasebythe ellagitannins oenothein A and oenothein B from *Epilobium* species. "Planta Med. (1977), 63(2), 111-114.
4. Ducrey et al. (1997). "Inhibition of 5-alpha-reductase and aromatase by the ellagitannins oenothein A and oenothein B from *Epilobium* species "Planta Medica, vol. 63(2): 111-114.
5. Hendry et al. "Iron-induced oxygen radical metabolism in waterlogged plants". HCAPLUS103:211253, New Phytol. (1985), 101 (1), 199-206.*
6. Hiermann (1987). "The investigation of active compounds from *Epilobium* species. 4th Communication. The antiinflammatory effect of different *Epilobium* species and their influence on prostaglandin "Scientia Pharamaceutica, vol. 55(2): 111-116.
7. Hiermann,et al. (1991), PlantaMedica, 57:357.
8. Juan et al. "Anti-inflammatory effects of a substance extracted from *Epilobium angustifolium*". Medline: 88180554 Agents and Actions, (1988 February) 23 (1-2), 106-
9. Kotaro (1997). "Anti allergy action of *Rubus suavissimus*" ChemicalAbstracts, vol. 127(9):52-59.
10. Lesuisse, D. et al. (1996), J Nat Prod, Determination of Oenothein Bas the Active 5-Alpha-Reductase-Inhibiting Principle of the Folk Medicine *Epilobium Parviflorum*,
11. Luepke, N. P. & Kemper, F. H., (1986), The HETCAM Test: An Alternative to the Draize Eye Test, Food and Chemical Toxicology,
12. Miyamoto, K., et al. (1993), J pn J Cancer Res, Antitumor Activity of Oenothein B., a Unique Macroyclic Ellagitannin, 84(1):99-103.
13. Okuda, T., Yoshida, T. & Hatano, T. (1989), Ellagitannins as Active Constituents of Medicinal Plants, Planta Med, 55(2):117-22.
14. Spielmann et al., (1997), CAM-based Assays, Food and Chemical Toxicology, 35:39-66.
15. Polyphenols from Bulgarian medicinal plants with antiinfectious activity. Ivancheva S; Manolova N; Serkedjieva J; Dimov V; Ivanovska N. Basic Life Sci, 590:717-28
16. A Kiss, J Kowalski, M F Melzig. Induction of neutral endopeptidase activity in PC-3cells
17. By an aqueous extract of *Epilobium angustifolium* L. and oenothein B. Affiliation: Department of Pharmacognosy, Medical University of Warsaw, and Warsaw, Poland. Kiss ankaat wp.pl) Journal Phytomedicine: International Journal of Phototherapy and Phytopharmacology (Phytomedicine) Vol. 13 Issue 4 Pg. 284-9 (March 2006)
18. Studies on antibacterial, anti-inflammatory and antioxidant activity of herbal remedies used in the treatment of benign prostatic hyperplasia and prostatitis. Steenkamp, Vanessa; Gouws, M. C.; Gulumian, M.; Elgorashi, E. E.; VanStaden, J. (2006)
19. Improved and Validated HPTLC Method for Quantification of Oenothein B and its Use for Analysis of *Epilobium angustifolium* L. Alexander N. Shikov*, Olga N. Pozharitskaya, Svetlana A. Ivanova, Valery G. Makarov, Vladimir P. Tikhonov, and Bertalan Galambosi
20. Immunomodulatory Activity of Oenothein B Isolated from *Epilobium angustifolium* Igor A. Schepetkin*, Liliya N. Kirpotina*, Larissa Jakiw*, AndreiI. Khlebnikov†, Christie L. Blaskovich*, Mark A. Jutila*, and Mark T. Quinn*, 2*Departments of Veterinary Molecular Biology, Montana State University, Bozeman, Mont. 59717 †Department of Chemistry, Altai State Technical University, Barnaul 656038, Russia
21. The vascular protective effects of estrogen. Farhat M Y[1], Lavigne M C, Ramwell P W
22. Phytochemistry, pharmacology and traditional uses of different *Epilobium* species. (Onagraceae) 2014, Kiss A
23. Assessment report on *Epilobium angustifolium* L. and/or *Epilobium Parviflum* Schreb., herba (Final) European Medicines Agency 2016
24. Topical Melatonin for treatment of Androgenic Alopecia
25. Androgenetic Alopecia-A Complex Disorder-with a Multilateral Treatment Strategy, 2017
26. Rational design of food-grade polyelectrolyte complex coacervate for encapsulation and oral enhanced oral delivery of oenothein B. Lan Y 2017
27. Prevalence and Trends of Urinary Incontinence in Adults in the United States, 2006-2010
28. Therapeutic Potential of Polyphenols from *Epilobium angustifolium* (Fireweed) Igor A. Schepetkin, Andrew G. Ramstead, Liliya N. Kirpotina, Jovanka M. Voyich, Mark A. Jutila, and Mark T. Quinn
29. Antibacterial activity of silver nanoparticles: A surface science insight, 2016, Benjamin Le Ouay Francesco Stellacci
30. Wikipedia (glycerol)

What is claimed is:

1. A method of treating an overactive bladder in a human female subject comprising administering to the subject a therapeutically effective amount of a composition consisting of oenothein A or B and a pharmaceutically acceptable carrier, wherein the overactive bladder is characterized by one or more symptoms selected from the group consisting of frequency or urgency, nocturia, increase in urinary micturition frequency, and urinary incontinence, thereby treating the overactive bladder.

2. The method of claim 1, wherein the oenothein A or B is formulated in an oral dosage form.

3. The method of claim 2, wherein the oral dosage form is a capsule or a liquid.

4. A method of treating urinary incontinence, comprising administering to a human female subject in need thereof a therapeutically effective amount of a composition consisting of oenothein A or B and a pharmaceutically acceptable carrier, thereby treating urinary incontinence.

5. The method of claim 1 or 4, wherein the oenothein is extracted or prepared from New World *Epilobium parviflorum* (small willow herb) and purified to a concentration of more than 10% by weight.

6. The method of claim 1 or 4, wherein the oenothein is extracted or prepared from a plant source other than New World *Epilobium parviflorum*.

* * * * *